United States Patent [19]

Tritsch

[11] 4,055,181

[45] Oct. 25, 1977

[54] TAPE CLOSURE HAVING RELEASE MEANS INTEGRAL WITH DIAPER BACKING SHEET

[75] Inventor: Ludwig Tritsch, Wilmette, Ill.

[73] Assignee: Johnson & Johnson, New Brunswick, N.J.

[21] Appl. No.: 655,181

[22] Filed: Feb. 4, 1976

[51] Int. Cl.² .............................................. A41B 13/02
[52] U.S. Cl. ..................................... 128/287; 128/284
[58] Field of Search ............ 128/287, 284, 286, 290 R

[56] References Cited

U.S. PATENT DOCUMENTS

| | | | |
|---|---|---|---|
| 3,848,597 | 11/1974 | Endres | 128/287 |
| 3,893,460 | 7/1975 | Karami | 128/284 X |
| 3,921,638 | 11/1975 | Schaar | 128/287 |
| 3,930,502 | 1/1976 | Tritsch | 128/284 X |
| 3,967,622 | 7/1976 | Cepuritis | 128/287 |

Primary Examiner—Stephen C. Pellegrino

[57] ABSTRACT

A disposable diaper having a facing sheet defining a diaper inside surface and a backing sheet defining a diaper outside surface is provided with adhesive tabs having an adhesive-coated face and a non-tacky opposite face. A fixed end of each tab is attached to a side marginal location of the diaper outside surface, and the opposite free end of each tab is adapted for folding back to a position wherein the non-tacky face of the free end is juxtaposed to the non-tacky face of the fixed end. A release means is provided on the diaper outside surface adjacent to the adhesive-coated face of the free end when folded back, and a portion of the diaper bearing the release means is adapted for folding thereover. The tabs are movable from a storage position, wherein the free end of each tab is folded back and a portion of the diaper is folded thereover to releasably adhere the adhesive-coated face of the free end to the release means, to an unfolded working position wherein the free end is available to secure the diaper about an infant and the release means remains on the diaper outside surface where it will not contact the infant's skin.

4 Claims, 10 Drawing Figures

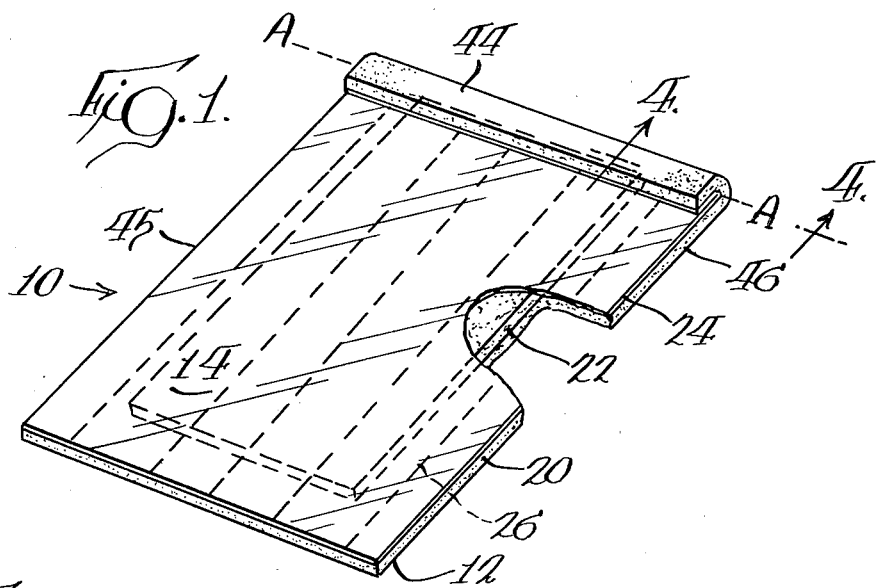
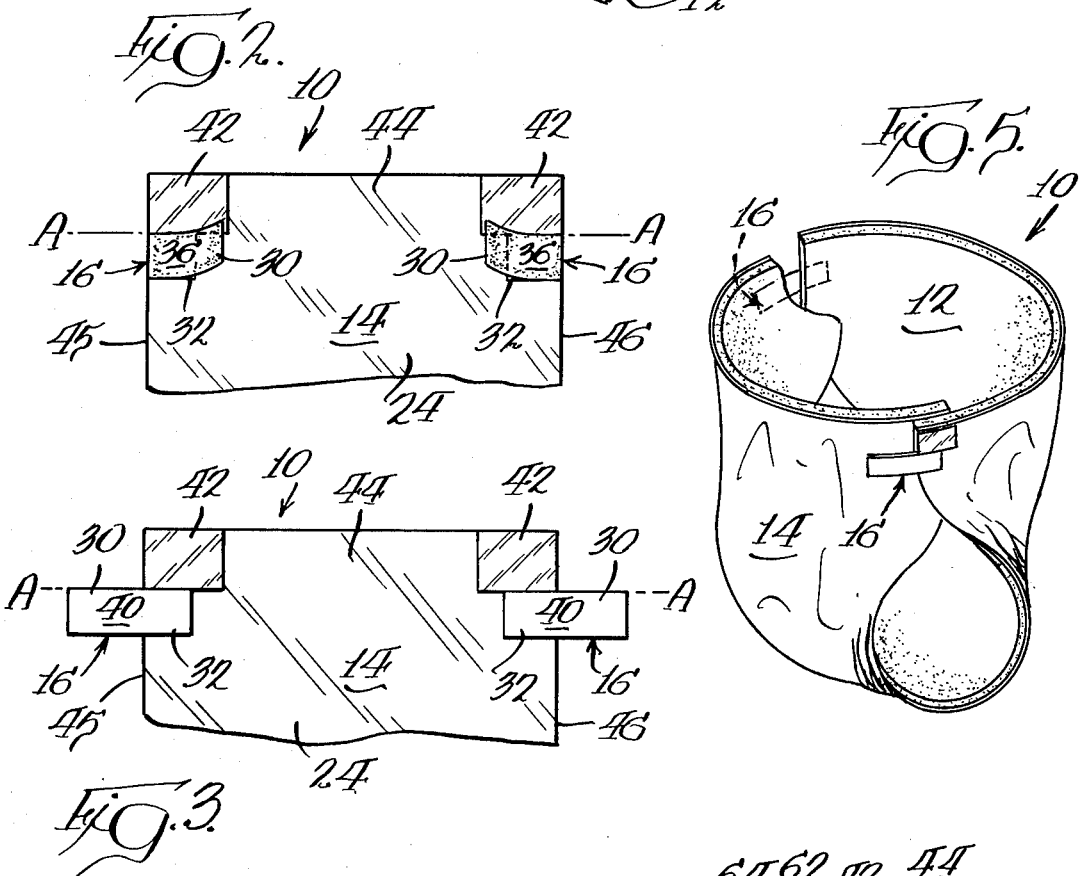
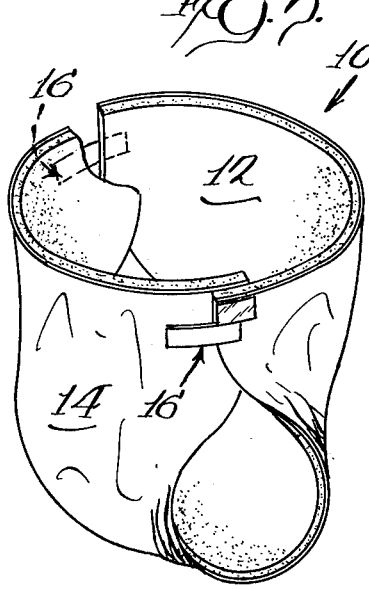

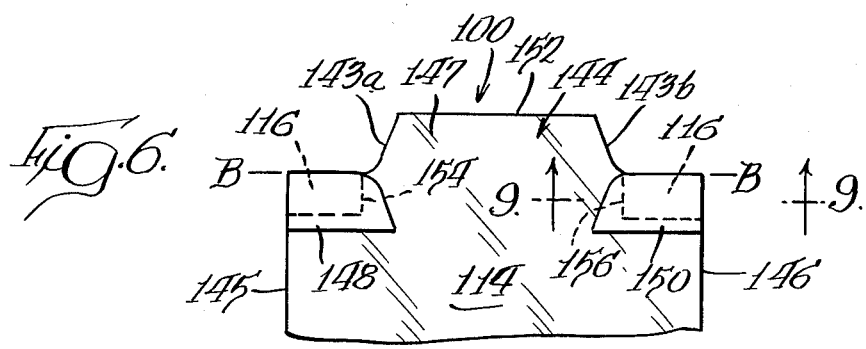
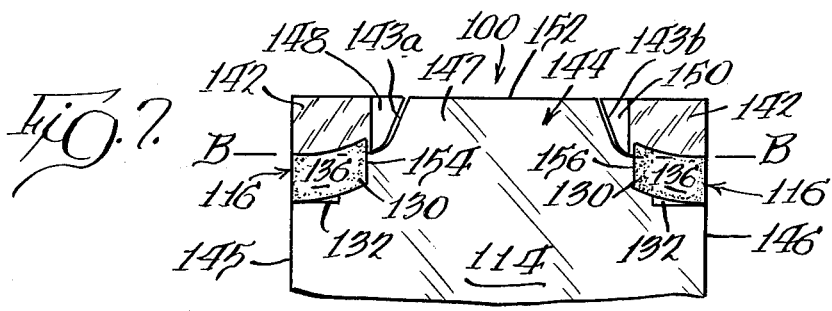
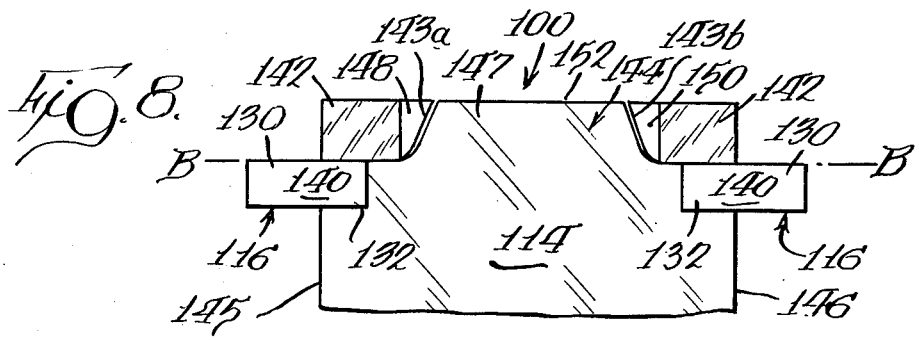
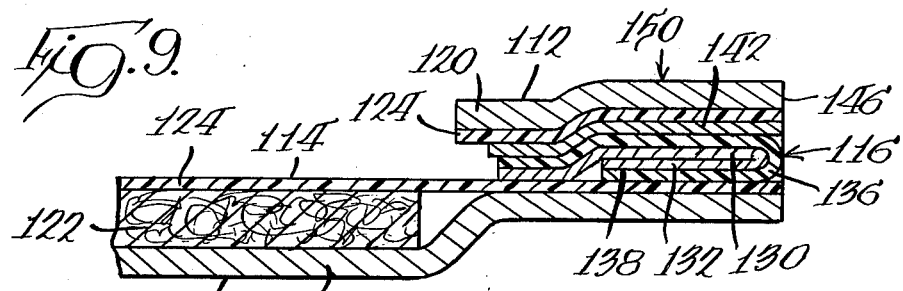
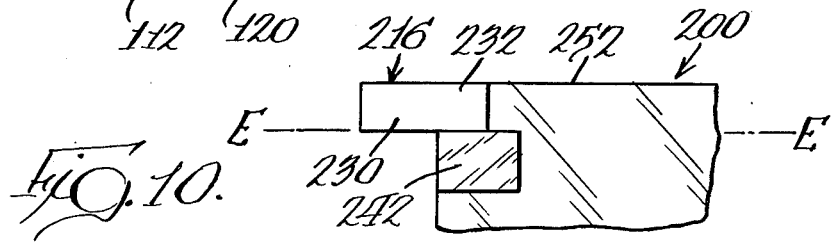

TAPE CLOSURE HAVING RELEASE MEANS INTEGRAL WITH DIAPER BACKING SHEET

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. Re26,151 to Duncan et al.

As may be seen from the above-cited patents, it is desirable to obviate the problems that are inherent in closure systems which utilize extraneous fasteners such as safety pins, snaps and zippers. To this end, adhesive closure systems have presented acceptable solutions.

In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper. Many prior art cover strips have the further disadvantage that the consumer must dispose of the cover strips when they are separated from the adhesive tabs. This is an inconvenience to the consumer who is positioning the diaper on an infant at the same time.

In an attempt to solve the foregoing problems, U.S. Pat. No. 3,646,937 to Gellert teaches a fastening tab which is provided with a release surface permanently bonded primarily to the inside surface of the diaper. One of the drawbacks of the Gellert arrangement is that the release surface is on the inside of the diaper where it can possibly come in contact with an infant's tender skin.

U.S. Pat. No. 3,921,638 to Schaar teaches a fastening tab which is folded over onto a release surface which is permanently bonded to the diaper. The release surface is transversely aligned with the tabs, and both longitudinal margins of the diaper are folded over in their entirety to cover the adhesive on the fastening tabs. In some of the embodiments, the release surface is on the front surface of the diaper, where it can possibly contact the infant's tender skin.

Commonly assigned U.S. patent application Ser. No. 539,554 by Tritsch, filed Jan. 8, 1975, discloses a structure wherein a release region is provided on the diaper outside surface. A relatively long adhesive tab is attached to the diaper outside surface, and the fixed end of the tab has a release coating to which the free end of the tab is releasably adhered.

SUMMARY OF THE INVENTION

According to the present invention, tape tabs that are used on each side of the diaper to secure the diaper about an infant are protected by folding thereover a portion of one of the diaper transverse margins when in the storage position. The diaper includes a facing sheet defining a diaper inside surface, a moisture-impervious backing sheet defining a diaper outside surface, and an absorbent panel positioned between the facing sheet and backing sheet.

Each tab comprises an elongated tape segment having one face provided with an adhesive coating and a non-tacky opposite face. One end of the tape segment is a fixed end attached to a longitudinal side marginal location of the diaper outside surface, and the opposite free end of the tape segment is adapted for folding back to a position wherein the non-tacky face of the free end faces the non-tacky face of the fixed end.

A release means is provided on the diaper outside surface adjacent the fixed end of the tape segment. Preferably, the release means is situated near a diaper margin, and at least a portion of the margin is adapted for folding back upon itself about a fold line extending between the release means and the folded-back free end. Alternatively, the diaper margin carrying a folded-back tab free end can be folded over the release means, In either case, the diaper assumes a folded storage position wherein the free end of the tape segment is folded back and juxtaposed to the fixed end and the diaper is folded so that an adhesive-coated face of the free end is releasably adhered to the release means. The diaper is movable from the storage position to an intermediate position wherein the diaper is unfolded and the free end of the tape segment is still folded back, but separated from the release means, and then to an unfolded working position wherein both the diaper margin and the free end of the tape segment are unfolded and the free end is available to secure the diaper about an infant.

The adhesive-coated surface on the free end of the tape tab fastener of the present invention is pressure-sensitive and is covered and positioned in a protected location within the confines of the folded diaper to use. Another advantage is that the release means remains on the diaper outside surface where it is out of contact with an infant's tender skin. Moreover, the tape tabs remain flat against the diaper when in the folded configuration and will not interfere with the diaper manufacturing machinery and the subsequent packaging operations.

BRIEF DESCRIPTION OF THE DRAWINGS

FIG. 1 is a perspective view, partially broken away to shown interior detail, of a folded diaper in accordance with one of the embodiments of this invention;

FIG. 2 is a fragmentary plan view of the fastener in accordance with one of the embodiments of this invention, with the diaper unfolded and the tab fastener folded back on itself;

FIG. 3 is a fragmentary plan view similar to FIG. 2 and showing the tab fastener in the open position;

FIG. 4 is an enlarged fragmentary cross-sectional view of the diaper of FIG. 1 taken along plane 4—4;

FIG. 5 is a perspective view, partially broken away, of the diaper of FIG. 1 in a configuration assumed by the diaper when placed about an infant;

FIG. 6 is a fragmentary plan view of a diaper in accordance with an alternate embodiment of the invention, with each tab fastener folded back on itself and a portion of the diaper folded back on the tab fasteners;

FIG. 7 is a fragmentary plan view, similar to FIG. 6, and showing the diaper unfolded and each tab fastener folded back on itself;

FIG. 8 is a fragmentary plan view, similar to FIGS. 6 and 7, and showing the diaper unfolded and the tab fasteners in the open position;

FIG. 9 is an enlarged fragmentary cross-sectional view of the diaper of FIG. 6 taken along plane 9—9; and FIG. 10 is a fragmentary plan view of the diaper in accordance with another embodiment of this invention.

DESCRIPTION OF THE PREFERRED EMBODIMENTS

In the following description, two digit numerals are used to refer to the embodiment illustrated in FIGS. 1-5, three digit numerals in the 100 series are used to refer to the embodiment illustrated in FIGS. 6-9, and three digit numerals in the 200 series are used to refer to the embodiment illustrated in FIG. 10. The same last two digits in each numeral designate similar elements in the various embodiments.

Disposable diaper 10, illustrated in FIGS. 1 and 5, is of substantially quadrilateral configuration and presents inside surface 12 for direction toward an infant and outside surface 14 for direction away from the infant. Adhesive tab fastener means such as tab 16 is attached to diaper 10 at a marginal location for securing diaper 10 about an infant. As described in greater detail below, a portion of diaper 10 is movable from a folded-over storage position illustrated in FIG. 1 wherein tab 16 is folded back on itself and a portion of the diaper is folded back over the tab, to an intermediate position illustrated in FIG. 2 wherein the diaper is unfolded and tab 16 is still folded back on itself, and ultimately to a working position which is illustrated in FIG. 3 wherein both diaper 10 and tab 16 are unfolded and tab 16 is ready for use.

Referring first to FIGS. 1 through 5, diaper 10 comprises moisture-pervious facing sheet 20 which defines diaper inside surface 12, overlying a moisture-retaining absorbent pad 22, and backing sheet 24 which is made of a moisture-impervious material and defines diaper outside surface 14. Absorbent pad 22 can be somewhat smaller than the backing sheet 24 and is centrally disposed thereon; however, absorbent pad 22 can be made coextensive with backing sheet 24, if desired. Facing sheet 20 is substantially coextensive with backing sheet 24. Both facing sheet 20 and pad 22 can be anchored to backing sheet 24 by means of adhesive beads 26, glue spots or in any other convenient manner. For example, if backing sheet 24 is made of a thermoplastic material, facing sheet 20 and pad 22 can be attached thereto by heat bonding.

As illustrated in FIGS. 2 through 4, tab 16 is an elongated tape segment having free working end portion 30 and fixed end portion 32. Both free end 30 and fixed end 32 are provided with an adhesive coating on one face thereof. The adhesive coating may comprise continuous pressure-sensitive adhesive coating 36 on inner face 38 of tab 16. The opposite outer face 40 of tab 16 is non-tacky. Fixed end 32 is attached to a marginal location of the longitudinal side of diaper outside surface 14 by means of adhesive coating 36.

Release means 42 is carried by diaper 10 on outside surface 14 thereof and provides a release region adjacent to tab 16. Release means 42 is transversely offset from tab 16 and is at or near a corner of the diaper. The release means is adapted to releasably engage free end 30 when tab 16 is folded back and diaper 10 is folded thereover, as described in detail hereinbelow. During manufacture of diaper 10, free end 30 of tab 16 is folded back upon itself so that the non-tacky face of free end 30 is juxtaposed to the non-tacky face of fixed end 32, as shown in FIGS. 2 and 4. Transverse margin 44 of diaper 10 extends between diaper side edges 45, 46. At least a portion of margin 44 is adapted for folding back upon itself about a fold line A—A which extends between release means 42 and the free end 30 of tab 16 when free end 30 is folded back. Diaper 10 thereby assumes the configuration illustrated in FIGS. 1 and 4 wherein adhesive coating 36 along free end 30 is releasably adhered to release means 42 in juxtaposition therewith. Thus, the entire tab 16 is tucked within diaper 10 simply by folding one transverse margin of the diaper. In this position, tab 16 will not interfere with machinery during manufacture of the diaper. It is a further feature of the present invention that release means 42 remains on the outside surface 14 of the diaper where it is out of contact with an infant's tender skin.

In the embodiment illustrated in FIGS. 1 through 5, transverse margin 44 which carries release means 42 and is adapted for folding back is an end marginal portion of diaper 10. In this particular embodiment, the entire end margin 44 between diaper side edges 45, 46 is adapted for folding back so as to extend over the adhesive coatings 36 along folded-back free ends 30 of a pair of tape tabs 16 attached to opposing side margins of diaper 10.

In the embodiment illustrated in FIGS. 6 through 9, diaper 100 is provided with a pair of opposed tabs 116 having free end 130 and fixed end 132. Adhesive coating 136 is provided on inner face 138 of tabs 116, but outer face 140 of tabs 116 is non-tacky. Release means 142 is carried on outside surface 114 and provides a release region adjacent tab 116. Margin 144 is an end margin and is provided with a pair of slits 143a, 143b each of which is disposed inwardly of the diaper side edges 145, 146. The slits in margin 144 define middle segment 147 and a pair of flaps 148 and 150 which flank middle segment 147 and can be folded back about line B—B. Flaps 148, 150 carry release means 142 for releasably covering the adhesive-coated faces of free ends 130 when the tabs are folded back.

Diaper 100 assumes the configuration illustrated in FIGS. 6 and 9 when tabs 116 are folded back and flaps 148, 150 are folded back thereover to cover the portion of adhesive coating 136 on free ends 130. To expose the portion of adhexive coating 136 on free ends 130 for fastening the diaper about an infant, the folded-back flaps 148, 150 are grasped and moved to an unfolded position, thereby exposing adhesive coatings 146 on the folded-back free ends 130 of tab 116, as shown in FIG. 7. Free ends 130 of the folded-back tabs 116 can be grasped to extend tabs 116 to the working position illustrated in FIG. 8. Slits 143a and 143b extend inwardly from transverse edge 152 of diaper 100, and may be normal to the transverse edge or arcuate. Preferably, flaps 148, 150 are of a larger area than the adhesive-coated face of free ends 130. The portions of flaps 148, 150 which extend outwardly beyond the edge 154, 156 of the adhesive-coated face of free ends 130 (FIGS. 6 and 7) comprise a gripping means for separating free ends 130 from release means 142 when fastening diaper 100 about an infant.

As depicted in FIG. 10, the relative position of tabs 216 and release means 242 in the embodiments illustrated in FIGS. 1 through 9 can be reversed. Thus, fixed end 232 can be situated between an adjacent transverse edge 252 of diaper 200 and release means 242. The embodiment of FIG. 10 is similar to the above-described embodiments in that tab 216 is folded back upon itself so that a non-tacky face of free end 230 is juxtaposed to a non-tacky face of fixed end 232, and at least a portion of margin 244 is folded back upon itself about fold line E—E extending between release means 242 and the folded-back free end 230 of tab 216 so that an adhesive-coated face of free end 230 is releasably adhered to release means 242.

Generally, release means 42 may comprise a ribbon segment or release strip carried on outside surface 14 of diaper 10 and provided with a release coated face 62 (FIG. 4) which provides the release region, and an adhesive coating on opposite face 64 by means of which the release strip is anchored to backing sheet 24. Release coated face 64 faces in the same direction as diaper outside surface 14 and is substantially coextensive with the portion of adhesive coating 36 on free end 30 of tab 16 when free end 30 is folded back. Alternatively, release means 42 may comprise a release coating, such as a silicone release compound, or the like, on the outside surface 14 of diaper 10 and which is substantially coextensive with the portion of adhesive coating 36 on free end 30 of tab 16 when free end 30 is folded back.

It is desirable to provide a gripping means to facilitate grasping tab 16 to separate free end 30 from release means 52 to unfold the diaper preparatory to fastening the diaper about an infant. Thus, as shown in FIG. 4, release means 42 may be provided with a longitudinal dimension greater than free end 30 of tab 16 to facilitate gripping the free end 30.

In all of the aforedescribed embodiments, folded-back free end 30 can be readily grasped to extend tab 16 to the working position because the non-tacky surfaces of free end 30 and fixed end 32 are juxtaposed to one another, and the pressure-sensitive adhesive coating 36 along free end 30 presents a tacky surface which faces outwardly.

Adhesive tabs suitable for the purposes of the present invention can be made from a wide variety of materials, provided that such materials are sufficiently flexible. Preferred materials for this purpose are polyalkylene webs such as polyethylene sheet, polypropylene sheet, and the like. Particularly preferred are webs which are oriented along the narrow dimension of the tab or webs which have filament reinforcements therein.

The pressure-sensitive adhesive layers such as adhesive coating 36 are provided by applying a coating of a pressure-sensitive adhesive composition known in the art to the appropriate surface of tab 16. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Anchored release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing shet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, nonwoven fabric which is formed, for example, in accordance with the teachings of commonly assigned U.S. Pat. Nos. 2,862,251, 3,081,514 and 3,081,515. Briefly, such fabrics are foraminous structures wherein group or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, facing sheet 20 can be formed of a non-apertured material, such as a nonwoven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by unfolding the diaper to expose the adhesive-coated face of the folded-back free end 30 by pulling margin 44 outwardly to separate free end 30 from its temporary engagement with release means 42. Free end 30 is then unfolded and extended to a working position. The tabs are then used to secure the diaper in the desired position by simply urging the pressure-sensitive adhesive surfaces in contact with the adjacent outer surface of the diaper. The applied diaper assumes the configuration illustrated in FIG. 5.

The foregoing description and the drawings are illustrative but are not to be taken as limiting. Still other variations and modifications are possible without departing from the spirit and scope of the present invention.

I claim:

1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:
   a pair of elongated tape segments each having: one face provided with an adhesive coating and a non-tacky opposite face, a fixed end attached to said diaper by means of said adhesive coating at a side marginal location of said outside surface, and a free end, said adhesive coating on said free end being pressure-sensitive, said free end being adapted for folding back so that the non-tacky face of said free end is juxtaposed to the non-tacky face of said fixed end and said adhesive-coated face of the free end faces in the same direction as said diaper outside surface;
   said diaper having a transverse margin which is provided with a pair of slits defining a middle segment of said transverse margin and flaps flanking said middle segment, each flap being situated next to one of said tape segments;
   release means provided on said flaps on said outside surface of said diaper and adjacent to said fixed end of each tape segment for releasably covering the adhesive-coated face of the folded back free end of each tape segment; and
   each flap being adapted for folding over said adhesive-coated face of the folded-back free end of said associated tape segment to releasably adhere said adhesive-coated face of each free end to said release means.

2. The disposable diaper as defined in claim 1 wherein said slits are substantially normal to the transverse edge of said diaper.

3. The disposable diaper as defined in claim 1 wherein said slits are arcuate and extend from the transverse edge of said diaper.

4. The disposable diaper as defined in claim 1 wherein said flaps are of a larger area than the adhesive-coated faces of said free ends and additionally provide a gripping means for separating said free ends from said release means.

* * * * *